(12) United States Patent
Wohltjen

(10) Patent No.: US 12,235,235 B2
(45) Date of Patent: Feb. 25, 2025

(54) SYSTEM AND METHOD FOR GAS CONCENTRATION MEASUREMENT

(71) Applicant: ENMET, LLC, Bowling Green, KY (US)

(72) Inventor: Henry Wohltjen, Bowling Green, KY (US)

(73) Assignee: Enmet, LLC, Bowling Green, KY (US)

( * ) Notice: Subject to any disclaimer, the term of this patent is extended or adjusted under 35 U.S.C. 154(b) by 910 days.

(21) Appl. No.: 17/239,255

(22) Filed: Apr. 23, 2021

(65) Prior Publication Data

US 2022/0341871 A1    Oct. 27, 2022

(51) Int. Cl.
    *G01N 27/414*    (2006.01)
    *G01N 33/00*    (2006.01)

(52) U.S. Cl.
    CPC ..... *G01N 27/4141* (2013.01); *G01N 33/0016* (2013.01); *G01N 33/007* (2013.01)

(58) Field of Classification Search
    CPC ........ G01N 21/88; G01N 21/85; G01N 21/94; G01N 27/4077; G01N 27/4118;
    (Continued)

(56) References Cited

U.S. PATENT DOCUMENTS 4,007,456 A    2/1977 Paige
4,627,269 A    12/1986 Forster
(Continued)

FOREIGN PATENT DOCUMENTS

DE    10245947 B4    1/2007
JP    2002318215 A    10/2002
(Continued)

OTHER PUBLICATIONS

Kreisl, P. et al., "Detection of hydrocarbon species using silicon MOS capacitors operated in a non-stationary temperature pulse mode" Sensors and Actuators B 106 (2005) pp. 489-497.
(Continued)

*Primary Examiner* — John Fitzgerald
*Assistant Examiner* — Truong D Phan
(74) *Attorney, Agent, or Firm* — Cittone Demers & Arneri LLP

(57) ABSTRACT

A system and method for ascertaining the concentration of a preselected target substance, characterized by a mitigated tendency for yielding results distorted by a departure from a state of calibration, i.e., by "drift", which drift is ordinarily caused by temperature and humidity variations; drift-mitigation is achieved by exposure of a target substance to a metal oxide semiconductor material, the temperature of a heating element operatively associated with said material being cycled between a low-temperature interval and a high-temperature interval, in which latter interval the material's temperature is raised to a level at or above the minimum temperature for rapid formation of one or more oxides of the target substance, the oxide formation taking place in a sufficiently short time that the conductivity is reflective of a transient signal amplitude in a brief interval of time, such that the external factors causing drift do not have sufficient opportunity to distort the concentration determination.

21 Claims, 2 Drawing Sheets

PULSED-MOS GAS SENSOR SYSTEM

(58) Field of Classification Search
CPC ....... G01N 2021/945; G01N 2021/745; G01N 23/20033; G01N 25/4826; G01N 2030/3053; G01N 2035/00346; G01N 27/123; G01N 27/124; G01N 33/007; G01N 7/16; G01N 27/4141; G01N 33/0016; H05B 1/0283

See application file for complete search history.

(56) References Cited

U.S. PATENT DOCUMENTS

| | | | |
|---|---|---|---|
| 6,742,382 | B2 | 6/2004 | Warburton |
| 7,276,745 | B2 | 10/2007 | Nakagawa |
| 8,043,566 | B2 | 10/2011 | Morris |
| 8,234,906 | B2 | 8/2012 | De |
| 9,182,366 | B2 | 11/2015 | Izawa |
| 9,964,513 | B2 | 5/2018 | Matsuoka |
| 2004/0055899 | A1 | 3/2004 | Morris |
| 2005/0063873 | A1 | 3/2005 | Morris |
| 2007/0011256 | A1 | 1/2007 | Suzuki |
| 2018/0335411 | A1 | 11/2018 | Zanella |
| 2020/0088667 | A1* | 3/2020 | Passaniti .............. G01N 33/007 |
| 2022/0120702 | A1* | 4/2022 | Udrea .................... G01N 27/18 |

FOREIGN PATENT DOCUMENTS

| | | |
|---|---|---|
| JP | 3792016 B2 | 6/2006 |
| JP | 2009175153 A | 8/2009 |
| JP | 4996536 B2 | 8/2012 |
| WO | 2018209296 A1 | 11/2018 |

OTHER PUBLICATIONS

Muller, G. et al., "High-temperature operated field-effect gas sensors" Encyclopedia of Sensors (2006) pp. 431-458.

Kang, B. S. et al., "AlGaN/GaN-based metal "oxide" semiconductor diode-based hydrogen gas sensor" Applied Physics Letters 84.7 (2004) pp. 1123-1125.

Polyakov, Mykola et al., "Hydrocarbon reactions on MoS2 revisited, I: Activation of MoS2 and interaction with hydrogen studied by kinetic experiments" Journal of Catalysis 256.1 (2008) pp. 126-136.

Moos, Ralf, et al., "Solid state gas sensor research in Germany 'a status report'", Sensors 9.6 (2009) pp. 4323-4365.

* cited by examiner

SYSTEM AND METHOD FOR GAS CONCENTRATION MEASUREMENT

FIELD OF THE INVENTION

The present invention relates to a system and method for measuring concentration of a gaseous (including without limitation vaporous) target substance wherein potential inaccuracy due to "drift" is mitigated. The desired effect is attained by alternating the temperature of a metal oxide semiconductor material, in the presence of a target substance, between (a) a temperature under that at which target substance adsorbed on the metal oxide semiconductor material undergoes rapid oxide formation, and (b) a temperature at or above which the target substance undergoes rapid oxide formation. The conductivity of the metal oxide semiconductor material is a function of the amount of temperature-induced oxidation of a target substance adsorbed on said material. Exposure of the metal oxide semiconductor material, in the presence of a target substance, to a temperature at or above the one at which rapid formation of oxide occurs causes a spike in the conductivity of said material in a time sufficiently short that drift is foreclosed. This invention provides a system and method that permits the accurate measurement of target substance concentrations, without inaccuracies introduced by "drift", especially under circumstances in which re-zeroing and/or re-calibration of the sensor response is not possible.

BACKGROUND OF THE INVENTION

The sensing of chemical vapors and gases is important to many *desiderata* such as environmental monitoring, process control, and hazardous atmosphere alarms.

Metal oxide semiconductor (or "MOS") gas sensors are based on measurement of the electrical conductivity of a metal oxide semiconductor. When the semiconductor is heated to several hundred degrees centigrade, hydrocarbon vapors that come into contact with the hot semiconductor surface will be oxidized by oxygen atoms adsorbed on the MOS surface and the device's electrical conductivity will change.

MOS gas sensors are very well known and have been commercially available from numerous manufacturers for more than fifty years. Most are operated in a fashion where an integral heating element is continuously powered to provide a constant operating temperature of several hundred degrees, while the electrical conductivity of the MOS element is continuously measured to provide an indication of the presence or absence of hydrocarbon gases.

Semiconductors exhibit a thermally activated electrical conductivity. When the temperature of a semiconductor is increased, then its electrical conductivity also increases. The electrical conductivity changes of MOS gas sensors proceed vigorously when the MOS device is hot. When the device is not heated, hydrocarbon vapors in the vicinity of the MOS surface will adsorb but will not be rapidly oxidized. Applying heat to a cooled MOS device will produce an initial transient signal that is significantly larger than the steady-state signal due to the higher concentration of hydrocarbon molecules that collect without being oxidized on the cooled MOS surface. The transient signal is due to the "burn-off" of the enhanced hydrocarbon concentration as the MOS device heats up.

In zero air, there is no transient signal produced. Instead, the signal moves from a very low value typical of a cold semiconductor, to a steady-state value characteristic of the bulk conductivity of the hot metal oxide semiconductors, and back. However, in the presence of a hydrocarbon gas, which is adsorbed on a cooled MOS material, an increase in the MOS material's temperature causes the adsorbed gas to burn-off at a very high rate until the excess of adsorbed substance is depleted and ultimately conductivity converges back to a steady-state value that is significantly higher than the steady state value observed in zero air.

The burn-off coincides with a spike an conductivity reflected as a transient signal, which is known to be very reproducible and can readily be sensed. MOS gas sensor heater pulsing has been explored extensively as a way to enhance the performance of MOS gas sensor arrays intended for use in "e-nose" applications for the identification of hydrocarbon vapors. The shape of the transient signal is affected by the oxidation kinetics of the particular hydrocarbon exposed to the sensor and careful analysis of the transient signal properties can be used to distinguish one hydrocarbon from another.

While attractive however, MOS gas-sensor technology has seemed limited. More specifically, MOS gas sensors are subject to inaccuracy because of the effect of "drift", which refers to the migration away from an initial calibration over time and/or due to external factors. As a consequence, while there are many MOS sensors sold for quantitative gas measurement, they are disadvantageous because they need to be re-zeroed frequently due to drift in the readings caused by ambient temperature and humidity variations. And, while there is a body of literature that describes the use of thermally modulated MOS gas sensors, the purpose of the thermal modulation has been to provide signal artifacts that allow the MOS sensor and associated pattern recognition software to provide better identification of hydrocarbon vapors. None of the literature explored to date teaches anything about thermal modulation of an MOS gas sensor for the purpose of zero-drift reduction. Thus:

In U.S. Pat. No. 3,906,473 the inventor describes the use of different heater temperatures to discriminate between different gas types. It does not teach anything about zero-drift reduction.

In U.S. Pat. No. 4,399,684 the inventors describe the use thermal cycling to produce "signature patterns" for different gases. It does not teach anything about zero-drift reduction.

In U.S. Publication No. 2002/0168772 the inventors describe the use of different heater temperatures to determine if an MOS gas sensor has been "poisoned". It does not teach anything about zero-drift reduction.

No published references that discuss the utility of thermally pulsed or modulated MOS gas sensors for zero-drift reduction have been found.

Notwithstanding the evolution of sensor technology as discussed in the preceding paragraphs, there persists a need to measure the concentration of a target substance substantially free of inaccuracies introduced by drift from the initial calibrated state over time and/or due to external influences.

SUMMARY OF THE INVENTION

One objective of the invention is to provide a system and method for accurate determination of a target substance concentration, substantially free of inaccuracies which would otherwise be introduced over time and/or through external influences.

A further objective of the invention is to provide a system and method for determining the concentration of a preselected target substance without suffering the effects of substantial drift from an initially calibrated state.

Another objective of the invention is to provide a system and method as aforesaid for affording a determination of a preselected target substance which is quantitative.

The foregoing objects are achieved by practice of the invention as hereinafter described.

Accordingly, the invention involves deployment of cycled heating/cooling of MOS gas sensors to mitigate the effects of sensor-drift on the determination of a target substance's concentration, rather than to develop a qualitative profile of various substances, in respect of which drift is not a crippling problem.

In one aspect of the invention, a sensor system for ascertaining the concentration of a preselected target substance, said system having a mitigated tendency for yielding results distorted by the departure from a state of calibration, which comprises a metal oxide semiconductor material which is interactive with said preselected target substance, whereby when said material reaches a certain temperature there is a rapid formation of oxides of the target substance;

an element, in operative association with the metal oxide semiconductor material, which element is capable of giving off heat energy sufficient to cause the metal oxide semiconductor material to reach or exceed said certain temperature;

circuitry for emitting a signal at a predetermined time which initiates the powering of the element to increase its output of heat energy such that the temperature of the metal oxide semiconductor material increases from one below said certain temperature to one at or above said certain temperature, and for further emitting another signal at a subsequent predetermined time, which other signal initiates the depowering of the element to decrease its output of heat energy such that the metal oxide semiconductor material's temperature is permitted to decrease from one at or above said certain temperature to one below said certain temperature, the duration elapsing while the metal oxide semiconductor material is below said certain temperature being such that if present target substance is adsorbed on said metal oxide semiconductor material in an amount effective to support said rapid oxidation formation, and the duration elapsing while the metal oxide semiconductor material is at or above said certain temperature being such that adequate opportunity is afforded for said rapid oxide formation to occur;

circuitry for detecting a signal representative of the conductivity of the metal oxide semiconductor material during the time the temperature of said material is below said certain temperature, and for detecting another signal representative of the conductivity of the metal oxide semiconductor material during the time the temperature of said material is at or above said certain temperature; and circuitry for performing a differential comparison of said respective detected signals to derive a further signal representative of the target substance concentration.

In another aspect, the invention is in a method of mitigating the distortion of results from a sensor system for ascertaining the concentration of a preselected target substance, said distortion stemming from the sensor system's departure from a state of calibration, which comprises providing a metal oxide semiconductor material which is interactive with a preselected target substance, whereby when said material reaches a certain temperature there is a rapid formation of oxides of the target substance;

further providing an element, located in operative association with the metal oxide semiconductor material, which element is capable of giving off heat energy sufficient to cause the metal oxide semiconductor material to reach or exceed said certain temperature; and enabling a determination of the target substance's concentration through (i) interconnection of the element with circuitry for emitting a signal at a predetermined time, which signal initiates the powering of the element to increase its output of heat energy such that the temperature of the metal oxide semiconductor material increases from one below said certain temperature, and for further emitting another signal at a subsequent predetermined time, which other signal initiates the depowering of the element to decrease its output of heat energy such that the metal oxide semiconductor material's temperature is permitted to decrease from one at or above said certain temperature to one below said certain temperature, the duration elapsing while the metal oxide semiconductor material is below said certain temperature being such that if present target substance is adsorbed on said metal oxide semiconductor material in an amount effective to support said rapid oxidation formation, and the duration elapsing while the metal oxide semiconductor material is at or above said certain temperature being such that adequate opportunity is afforded for such rapid oxide formation to occur;

(ii) interconnection of the metal oxide semiconductor material with circuitry capable of detecting a signal provided during the time the temperature of the metal oxide semiconductor material is below said certain temperature, and for detecting another signal representative of the conductivity of the metal oxide semiconductor material during the time the temperature of said material is at or above said certain temperature; and (iii) interconnection of said detection circuitry with circuitry capable of performing a differential comparison of said respective detected signals to derive yet another signal representative of the target substance concentration.

And, in yet a further aspect, the invention is in a method of mitigating the distortion of results from a sensor system for ascertaining the concentration of a preselected target substance, which distortion stems from the sensor system's departure from a state of calibration, said sensor system including a metal oxide semiconductor material which is interactive with said preselected target substance at or above a certain temperature resulting in rapid formation of one or more oxides of said target substance, whereby a change in conductivity of the material also occurs, which method comprises contacting said metal oxide semiconductor material with said preselected target substance;

at a predetermined time during the contact between the metal oxide semiconductor material and the preselected target substance, heating said material such that its temperature increases from one below said certain temperature to one at or above said certain temperature, the duration elapsing while the material is below said certain temperature being such that if present target substance is adsorbed on said metal oxide semiconductor material in an amount effective to support said rapid oxide formation;

at a subsequent predetermined time during the contact between the metal oxide semiconductor material and the preselected target substance permitting the temperature to decrease from one at or above said certain temperature to one below said certain temperature, the duration elapsing while the material is at or above said certain temperature being such that adequate opportunity is afforded for said rapid oxide formation to occur;

generating a signal representative of the conductivity of the metal oxide semiconductor material while the material is below said certain temperature;

generating another signal representative of the conductivity of the metal oxide semiconductor material while the material is at or above said certain temperature;

detecting the conductivity-representative signal generated while the material's temperature is below said certain temperature;

detecting the conductivity-representative signal generated while the material's temperature is at or above said certain temperature; and performing a differential comparison of said respective detected signals to derive a further signal representative of the target substance concentration.

In a more specific aspect, the invention is in a sensor system for ascertaining the concentration of a preselected target substance, said system having a mitigated tendency for yielding results distorted by the departure from a state of calibration, which comprises a sensor including a metal oxide semiconductor material, which material is interactive with said preselected target substance at a minimum temperature resulting in rapid formation of one or more oxides of said target substance, whereby a change in conductivity of the material also occurs;

an element for heating the metal oxide semiconductor material, said element being located such that it is capable of bringing about a modulation of the material's temperature from one at which said rapid formation of oxides does not take place, to one at or above said minimum temperature at which rapid oxide formation does take place;

circuitry for emitting a signal at a predetermined time, which signal initiates manipulation of said heating element's behavior to modulate said material's temperature from one at which rapid oxide formation does not take place to one at or above said minimum temperature at which rapid oxide formation does take place, such that a precursor mode of sensor operation endures up until the time said material's temperature reaches the minimum one at which rapid oxide formation takes place, and for further emitting another signal at a subsequent predetermined time, which other signal manipulates said heating element's behavior to permit said material's temperature to decrease below the minimum one at which rapid oxide formation takes place, such that a measurement mode of sensor operation endures up until the time said material's temperature decreases below the one at which rapid oxide formation takes place, the material's being capable of temperature change sufficiently rapid that the duration elapsing between said predetermined time and said subsequent predetermined time can be short enough that the effect of any substantial departure from the sensor system's state of calibration is obviated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid formation of oxides and a corresponding increase in conductivity of the metal oxide semiconductor material to take place;

circuitry for detecting a signal representative of the conductivity of the metal oxide semiconductor material during the precursor mode of sensor operation, and for detecting another signal representative of the conductivity of said material during the measurement mode of sensor operation; and circuitry for performing a differential comparison of said respective detected signals to derive a further signal representative of the target substance concentration.

In another more specific aspect, the invention is in a method of mitigating the distortion of results from a sensor system for ascertaining the concentration of a preselected target substance, said distortion stemming from the sensor system's departure from a state of calibration, which comprises providing a metal oxide semiconductor material, which material is interactive with said preselected target substance at a minimum temperature resulting in rapid formation of one or more oxides of said target substance, whereby a change in conductivity of the material also occurs;

further providing an element for heating the metal oxide semiconductor material, said element being located such that it is capable of bringing about a modulation of the material's temperature from one at which said rapid oxide formation does not take place, to one at or above said minimum temperature at which rapid oxide formation does take place;

enabling a determination of the target substance's concentration through (i) interconnection of the heating element and circuitry configured to emit a signal at a predetermined time, which signal initiates manipulation of said heating element's behavior to modulate said material's temperature from one at which rapid oxide formation does not take place to one at or above said minimum temperature at which rapid oxide formation does take place, such that a precursor mode of sensor operation endures up until the time said material's temperature reaches the one at which rapid oxide formation takes place, and for further emitting another signal at a subsequent predetermined time which other signal initiates manipulation of said element's behavior to permit said material's temperature to decrease from one at or above which rapid oxide formation does take place to one at which rapid oxide formation does not take place, such that a measurement mode of sensor operation endures up until the time said material's temperature decreases below the one at which rapid oxide formation takes place, the material's being capable of temperature change sufficiently rapid that the duration of time elapsing between said predetermined time and said subsequent predetermined time can be short enough that the effect of any substantial departure from the sensor system's state of calibration is obviated, the duration of said precursor mode being such that if present target substance is adsorbed on said metal oxide semiconductor material in adequate amount to support said rapid oxidation formation at said minimum temperature, and the duration of said measurement mode being sufficient that adequate opportunity is afforded for said rapid oxide formation and a corresponding increase in conductivity of the metal oxide semiconductor material to occur;

(ii) interconnection of said metal oxide semiconductor material and said power source, or an alternative power source, whereby to generate current in, and provide a signal representative of the conductivity of the metal oxide semiconductor material during the precursor mode of sensor operation, and generate a current in, and provide a further signal representative of the conductivity of said material during the measurement mode of sensor operation;

(iii) interconnection of said material with circuitry capable of detecting the signal provided during the precursor mode of sensor operation, and the further signal provided during the measurement mode of sensor operation; and (iv) interconnection of said detection circuitry with circuitry capable of performing a differential comparison of said respective detected signals to derive yet another signal representative of the target substance concentration.

And in yet a further more specific aspect, the invention is in a method of mitigating the distortion of results from a sensor system for ascertaining the concentration of a preselected target substance, which distortion stems from the sensor system's departure from a state of calibration, said sensor system including a metal oxide semiconductor material which is interactive with said preselected target substance at a minimum temperature resulting in rapid formation of one or more oxides of said target substance, whereby a change in conductivity of the material also occurs, which method comprises contacting said metal oxide semiconductor material with said preselected target substance;

at a predetermined time during the contact between the metal oxide semiconductor material and the preselected target substance, heating said material such that its temperature is modulated from one below the minimum temperature at which rapid oxide formation occurs to one at or above said minimum temperature at which rapid oxide formation occurs for a period sufficient that rapid oxidation of the target substance is effected, such that a precursor mode of sensor operation endures up until the time said material's temperature reaches the one at which rapid oxide formation takes place, and at a subsequent predetermined time during the contact between the metal oxide semiconductor material and the preselected target substance permitting the temperature of said material to modulate from one at or above said minimum temperature at which rapid oxide formation occurs to one less than the minimum temperature at which rapid oxide formation occurs, such that a measurement mode of sensor operation endures up until the time said material's temperature decreases below the one at which rapid oxide formation takes place, the material's being capable of temperature change sufficiently rapid that the duration elapsing between said predetermined time and said subsequent predetermined time can be short enough that the effect of any substantial departure from the sensor system's state of calibration is obviated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid oxide formation and a corresponding increase in conductivity of the metal oxide semiconductor material to occur;

generating a signal representative of the conductivity of the metal oxide semiconductor material during the precursor mode of sensor operation, and another signal representative of the conductivity of the metal oxide semiconductor material during the measurement mode of sensor operation;

detecting the signal generated during the precursor mode of sensor operation, and the other signal generated during the measurement mode of sensor operation; and performing a differential comparison of said respective detected signals to derive a further signal representative of the target substance concentration.

Practice of the invention confers substantial advantages. Thus, while use of MOS sensor technology to derive the identity of a hydrocarbon unknown may have occurred, the technology was not used to secure concentration determinations. Deployment of such technology for quantitation of a target substance innovatively characterizes the present invention. Quantitation is achieved via generation of a transient signal—i.e., a high amplitude signal, which jumps to its maximum in a brief time span and correlates with a spike in conductivity of the MOS material. The spike in conductivity is the result of a rapid formation of oxides of the target substance adsorbed on such MOS material and is brought about via exposure of the MOS material to a temperature at or above which rapid formulation of oxides occurs. The material's conductivity is a function of the concentration of the target substance. And the rapidity of oxide formation causes the spike in conductivity in a brief period of time, which preempts the opportunity for inaccuracy over time (i.e., drift) to creep into the measurements entailed by the invention's practice. The invention is especially helpful in making reliable measurement of target substance concentration in situations where re-zeroing or other recalibration of an MOS gas sensor is complicated or precluded by the sensor's inaccessibility. It follows that troublesome periodic re-zeroing or other recalibration operations can be minimized (if not eliminated) without a meaningful sacrifice of consistency. And the invention is further desirable in that it involves as some of its elements already available (though repurposed) MOS gas sensor technology; moreover, the invention can be implemented using commercially available components, which tends to conserve on cost.

DETAILED DESCRIPTION OF CERTAIN PREFERRED EMBODIMENTS

Figure 1:
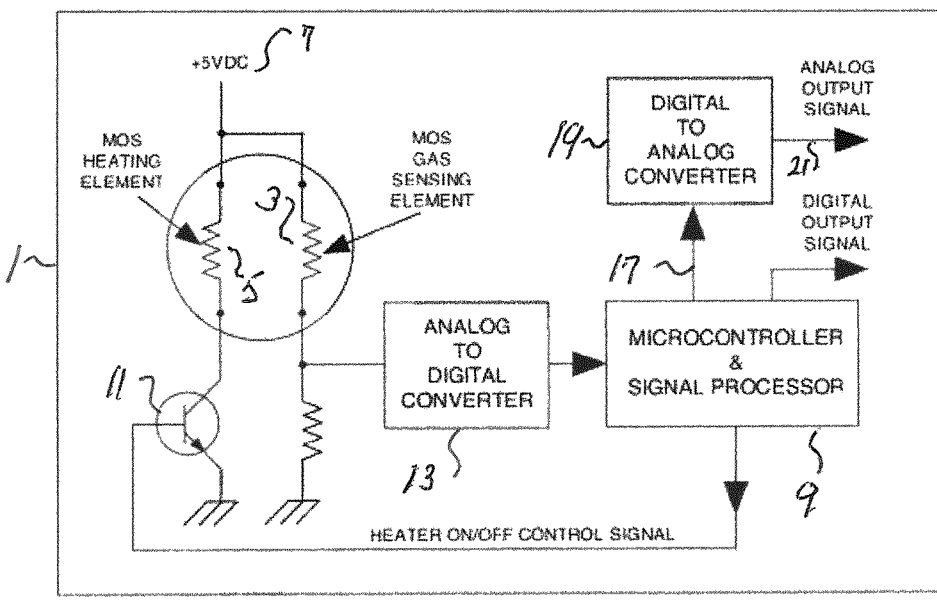
FIG. 1 is a schematic drawing of a sensor system in accordance with the invention, suitable for practice of a method in accordance with the invention.

While utilizing pulsed MOS gas sensor heating, the present invention is not concerned with the identification of unknown chemical vapors. Instead, it is focused on the accurate quantitation of a known gaseous substance, especially when it is prohibitively difficult to eliminate sensor zero-drift by periodically exposing the sensor to zero air and readjusting the zero setting of the sensor. Thus, the invention is in the discovery that sequential heating and cooling of an MOS material, i.e., thermal cycling, induces a concentration-dependent conductivity signal. The amplitude of the signal yields sufficient information for ascertaining concentration, without suffering the drift problem herein described.

MOS gas sensor zero-drift is a type of noise that exhibits slowly varying signals which have been correlated with temperature, pressure, and humidity variations, as well as aging of the sensor. A significant electronic component of zero-drift is called "flicker noise", the magnitude of which is proportional to $1/f$ (where f is the frequency of the signal). The measurement of slowly varying gas concentrations (e.g., over a period of days, weeks, and months) leads to very large measurement periods (t), very small values of "f" (since, $f=1/t$) and correspondingly high values of $1/f$. That is, the longer the interval between zero adjustments of the sensor, the greater the amount of zero drift that is likely to be observed.

The problem becomes especially acute when measurements are to be made over a long period of time. Uncompensated zero-drift can significantly degrade measurement accuracy. Ordinarily, long-term sensor zero-drift is compensated by periodically re-zeroing and re-calibrating the sensor response with appropriate gas samples. However, there are many scenarios that require the sensors be placed in locations that make it prohibitively difficult (or impossible) to perform periodic re-zeroing and re-calibration of the sensors.

The invention disclosed herein provides a system and method to reduce the effects of sensor zero-drift on the accuracy of MOS gas sensor measurement of concentration. This is done by cycling the temperature of the MOS material between a sub-rapid oxidation level and a temperature level at or above that required for rapid formation of oxides whereby to generate a transient signal representative (after any necessary or desired adjustment) of the material's conductivity. That data can be carried through processing (including comparison with a signal representative of the MOS material's conductivity at a sub-rapid oxide formation temperature) to yield a reliable concentration signal not meaningfully distorted by zero-drift because it is measured in such a short period of time.

Cycling of the element for heating the MOS material results in cycling of the temperature, and therefore the conductivity, of the MOS material. The changes in conductivity of the MOS material induce changes in the operational mode of the sensor. Thus, when the MOS material's conductivity is lower because the material's temperature is below the minimum temperature for rapid oxide formation, the sensor behaves in a "precursor mode". In such mode, the conductivity signal has a relatively lower amplitude up until the MOS material's temperature reaches a certain temperature (for instance the minimum temperature) at which rapid oxide formation occurs. The lower-amplitude output of the MOS material, characteristic of its behavior at temperature below that of rapid oxide formation, is conducted to the sensor's detection circuitry and processing circuitry. However, when the MOS material's conductivity suddenly jumps to a relatively higher level because the temperature reaches or exceeds that at which rapid oxide formation occurs, the signal observed likewise jumps, which is the phenomenon herein designated as the "transient signal". The reason is that, at the temperature of rapid oxide formation, the target substance adsorbed on the MOS material precipitously reacts with oxygen also present to form oxides. The MOS material has adsorbed on it a build-up of target substance, not yet oxidized due to the material's not yet having reached the minimum rapid oxide formation temperature, which promptly burns off once the temperature is attained and/or exceeded. The transient signal can be thought of as a spike, as its amplitude is temporarily augmented due to the burn-off of built-up adsorbed target substance. The transient signal is emitted during all or part of the time when the MOS material is at or above the aforementioned minimum temperature and continues while the reserve of adsorbed target substance endures, or until the reserve is exhausted. During the time of the MOS material's increased conductivity, the higher-amplitude output signal (i.e., transient signal), characteristic of the MOS material's behavior at or above the minimum temperature for inducing rapid formation of oxides (if sensed by the detection circuitry), is conducted to the sensor's detection circuitry and processing circuitry. And then, the output from the detection circuitry passes through to the processing circuitry where it is compared with the previously stored signal from a precursor mode. During the time the transient signal is being generated, the sensor is said to behave in a "measurement mode".

Environmental variability and 1/f flicker noise are significantly reduced by measuring the transient signal produced by an MOS gas sensor with a pulsed heating element. Unlike measurements of the steady-state signal over a period of months, the transient signal is measured over a brief time interval (e.g., seconds) during which temperature and other environmental conditions are effectively constant. The interval during which the temperature of the MOS material is below the aforementioned certain temperature (such as the temperature at which the rapid formation of oxides occurs) is referred to herein as a "cool" interval. The temperature during such "cool" interval can be from 0 to 100° C. The interval during which the temperature of the MOS material is at or above the temperature as aforesaid (e.g., the temperature of rapid oxide formation) is referred to herein as a "hot" interval. The temperature of the MOS during such "hot" interval can be from 250 to 400° C. The attainment of those temperatures during the "cool" and "hot" intervals results from configuration of the circuitry providing a signal to the heating element such the element's behavior is caused to bring about the desired temperature in the MOS material. Subsequently, a differential comparison of the signals produced by the MOS sensor during the "cool" and "hot" intervals of the measurement cycle provides a concentration measurement artifact that is far less affected by the zero-drift of the intrinsic MOS sensor operated in a steady-state manner. The approach results in a quasi-re-zeroing of the sensor with every measurement.

Beyond a focus on a different mode of operation wherein heating is alternately turned on and off, or temperature is varied between one below the minimum temperature for rapid formation of oxides and one at or above such minimum temperature, a central feature of the claimed invention is the generation of a transient signal which occurs in a sufficiently brief period of time that external environmental or other effects do not cause the signal measured to be distorted by drift. This is brought about by exploitation of the MOS material's exhibition of different amounts of conductivity depending on the temperature of the material. In accordance with the foregoing, the MOS material is utilized as a substrate upon which target substance can be adsorbed at a temperature below that at which rapid formation of oxides takes place. The target substance is then rapidly oxidized at a higher temperature. So, the MOS material's temperature is held below a certain one at which rapid oxidation of a target substance adsorbed thereon occurs, such as the aforementioned minimum temperature, and then the material's temperature is elevated to a point at or above that leading to the aforementioned rapid oxidation. The MOS material and the duration of time at which the sensor is in the precursor mode is enough that if present the target substance is adsorbed on the MOS material in sufficient amount that a transient signal can be generated during the measurement mode.

For its part, the duration of the measurement mode is long enough that the MOS material can reach a temperature at which rapid formation of oxides takes place. The MOS material, and the duration of the "hot" interval, are matched so that the measuring temperature for rapid formation of oxides is attained. This is precipitated by provision of an amount of power to the heating element sufficient to result in its giving off heat energy that induces the MOS material to reach (and in some embodiments to exceed) a certain temperature aligning with practice of the invention, such as the minimum temperature at which rapid formation of oxides of the target substance occurs. The build-up of target substance burns off due to attainment and maintenance thereafter of a temperature at or above the aforementioned certain temperature, whereby the conductivity of the MOS material abruptly rises, and preferably spikes. After a suitably short time, the temperature of the MOS material falls when the amount of power delivered to the heating element is decreased, so that the heat energy it emits also decreases, eventually (preferably quickly, especially in a period of 1-5 seconds) to one below the aforementioned certain temperature, especially the minimum temperature at which rapid formation of target substance oxides occurs, a temperature which depends on the nature of the target substance and of the MOS material. The conductivity levels of the MOS material are measured continuously during cycling of the heating element as aforesaid. The different conductivity values are determined and then converted (whether selectively or not) to counterpart signals that can be processed in appropriate circuitry which performs a differential comparison to generate a further signal that is representative of the target material's concentration.

Because the further signal derived through such differential comparison is based on a transient signal which can be sampled over an advantageously short period of time, the effects of external factors over time, which tend to distort the signal representative of the target substance concentration, are mitigated. Sensor systems and methods performed with them are calibrated against a standard so as to "zero" the system, such that measurements using the sensing technology of the invention remain substantially in conformity with the initially "zeroed" signal. Therefore, the signals which are derived from either readings over a single cycle, or over a series of cycles, are free of any material "zero drift" effects, and can be viewed as reliable through their having been made on a normalized basis due to zero drift's mitigation.

A key feature of the invention is the cycling of the heating element's operation, through cycling of the supply of power to the element. In this manner, the power supplied to the heating element is varied programmatically, whereby: (i) the power is off or supplied at a sufficiently low level that the MOS material's temperature remains below the above-mentioned certain temperature aligned with practice of the invention, such as the minimum temperature at which rapid formation of oxides occurs (that certain temperature either varying over time, or staying substantially constant is the nature of a "baseline" temperature) for a pre-selected period; (ii) thereafter the power is supplied at a higher level which is sufficient to induce the MOS material's being at or above such certain temperature; and (iii) the power is off, or supplied at a sufficiently low level, so that the MOS material is permitted to dip back down under such certain temperature again. The sequence of conditions (i) through (iii) can be referred to as a duty-cycle. In the present invention, the duty-cycle can be repeated a plurality, including a multiplicity, of times.

A further special aspect of the invention is the coordinating of the following to achieve practice of the invention:
(a) The identify of the target substance,
(b) The nature of the MSO material including (i) its capability of adsorbing the target substance at a temperature below a certain temperature aligning with practice of the invention, (ii) its capability of providing a reactor environment wherein adsorbed target substance is oxidized when the MOS material is at or above the aforementioned certain temperature (e.g., the temperature at which rapid function of oxides occurs), and (iii) its capability of temperature change sufficiently rapid that it can reach the aforementioned certain temperature as a result of the interval while heat energy is applied to the MOS material,
(c) the duration of the time for which the MOS material is below the aforementioned certain temperature, such that it is long enough for the target substance (if present) to be absorbed on the MOS material in sufficiently large amount that a detectable transient signal can be generated when the temperature is increased to one at or above such certain temperature,
(d) the duration of the time for which the MOS material is at or above the aforementioned certain temperature is sufficiently long that rapid formation of oxides and a corresponding conductivity of the MOS material can take place, and yet
(e) the duration of the time for which the MOS material is at or above such certain temperature is short enough that the effect of any substantial departure from the state of calibration is negated.

The duty-cycle's period is typically 20 seconds (though not exclusively, as the time period for the cycle can be 5 seconds, or up to 500, seconds more preferably 200 seconds). Correlatively, the components of the duty-cycle are: a low-temperature interval, wherein whether the temperature is substantially constant (e.g., a baseline temperature) or variable as long as it stays under the minimum temperature for rapid formation of oxides (a "cool" interval); a high-temperature interval (or "hot" interval) at or above the minimum temperature, and another low-temperature interval at a temperature below the minimum temperature for rapid formation of oxides. Those intervals can be ordered in the sequence low-temperature interval, high temperature interval, low-temperature interval. The high-temperature interval can range from a few (e.g., five) percent up through ninety percent of the duty-cycle. The first of the duty-cycle intervals (low-temperature) can be longer than the second (high-temperature); the third of the duty-cycle intervals (low-temperature) can be the same as the second. For instance, the first duty-cycle interval can be 10 seconds, the second duty-cycle interval 5 seconds, and the third duty-cycle interval 5 seconds. Typically, the duration of the respective intervals which make up the duty-cycle, arranged in the sequence low-temperature/high-temperature/low-temperature are in a ratio of from 2:1:1 to 4:1:4. Under conditions of continuous operation, the third and first duty-cycle intervals may overlap, or run into one another. Thus, there may not be any actual dividing line between the first and third duty-cycles, but they are conceptually delineated here for purposes of understanding. Ultimately, the second or high-temperature duty-cycle should be of sufficient duration that the aforementioned rapid formation of oxides has time to develop, but not so long that the distorting effects of external factors can manifest themselves to any appreciable extent.

It is essential to practice of the invention that the time interval for measuring conductivity at or above the minimum temperature for rapid formation of oxides be confined to a time not so great that the reliability of the measured signal—and the quantitation of the target substance's concentration based thereon—is compromised. Thus, the interval is diminished to a point that the distortive effects of elapsed time or external factors do not have sufficient opportunity to introduce inaccuracy to any meaningful extent. However, measuring the material's conductivity at or above the minimum temperature for rapid formation of oxides poses a further problem: how to conduct the requisite abbreviated measurement effectively. The solution is to produce a transient signal, i.e., signal of exceptionally high amplitude which manifests in the above-mentioned abbreviated time period. The combination of the foregoing elements is highly important to various embodiments of the invention.

It is also an important feature of various embodiments that the MOS material is interactive with the preselected target substance, and exhibits a measurable conductivity that changes with the material's temperature, as well as with a rise in temperature in a meaningfully short time so that its conductivity can be raised and measured before the influence of factors causing drift have a chance to affect measurements adversely. An MOS material is especially useful. MOS materials are, in and of themselves, known in the art. Suitable materials include type IV oxide compounds, which when exposed to oxygen at high temperature adsorb oxygen into the crystalline molecular matrix. The oxygen acts as an electron acceptor and reduces the electrical conductivity of the oxide. When the target substance is not present, a condition sometimes known as "zero-air", the MOS material's conductivity is relatively low. The target substance can be a reducing gas; when it contacts the surface of the detector, it is adsorbed and acts as an electron donor so as to reduce the resistance of the oxide body. As a result, the electric current flowing through the oxide body will increase above an initial value when the body is contacted by such reducing gases. When the oxide sensor is operated at a suitable temperature, an equilibrium is reached, producing a fixed equilibrium value of resistance. The temperature at which the aforementioned equilibrium state is attained is among those designated as a baseline temperature. See, also, U.S. Pat. No. 5,006,828 to Yutaka et al.; U.S. Pat. No. 4,958,513 to Yasunga et al.; U.S. Pat. No. 4,938,928 to Koda et al.; U.S. Pat. No. 4,827,154 to Naoyuki et al.; U.S. Pat. No. 4,718,991 to Yamazoe et al.; U.S. Pat. No. 4,701,739 to Sasaki; U.S. Pat. No. 4,658,632 to Sasaki; U.S. Pat. No. 4,575,441 to Murakami et al.; U.S. Pat. No. 4,459,577 to Murakami et al.; and U.S. Pat. No. 4,117,082 to Matsuyama. However, with the invention, a different dynamic is exploited. The temperature of the MOS material is driven up to or above a minimum temperature where target substance no longer exists at equilibrium on the material. Instead, at or above such minimum temperature the unoxidized target substance inventoried on the MOS material rapidly forms oxides via reaction with oxygen on the material. Due to the extra-high temperature of the MOS material, the conductivity very quickly attains a much higher temperature than one in which equilibrium occurs. Indeed, the burn-off of inventoried target substance causes a correlative rapid increase in conductivity within a comparable time frame, which is reflected as the transient signal as aforesaid. That signal can be utilized to quantitate target substance concentration.

The invention is unique because it is directed to the accurate measurement of the concentration of unwanted, and in some cases toxic, target substances, substantially undistorted by the adverse effects of "zero drift". The invention is especially useful for quantitating a hydrocarbon as the target substance. This includes alkanes, alkenes, alkynes and aromatics. The chief components of petroleum and natural gas are hydrocarbons. Examples of hydrocarbons are methane, ethane, propane, butane, isobutylene or other reducing gas. However, the nature of the target substance is not limited to the foregoing, as the invention is useful in the measurement of any gaseous substance which has a hydrogen-carbon bond, which adsorbs on the MOS material, and which is subsequently oxidized by locally present oxygen at a high rate (i.e., rapidly) when a temperature of sufficiently large magnitude is reached. Thus, in addition to hydrocarbons, the invention is useful in quantitating alcohols, aldehydes, ketones, acids, esters, ethers, cyclic species, whether saturated or unsaturated, and whether or not containing heteroatoms. Furthermore, the invention is useful in determining the concentration of hydrogen as a target substance. Hydrogen is a highly volatile substance which can be explosive, and it is thus important to detect it in undesirable concentrations. The MOS material is selected to be interactive with the target substance.

The minimum temperature for rapid formation of oxides depends on the specific composition of the MOS material. For common tin-oxide based materials the temperature typically ranges from 200° C. to 400° C., but may go as high as 600° C. Other metal oxide semiconductor materials have minimum temperatures for rapid formation of oxides that can be lower or higher depending on the material, such as up to 1000° C. Such minimum temperatures are conventionally derivable in and of themselves from information available in the public domain. Nevertheless, in the end each target substance has a particularized subrange of the aforementioned minimum temperatures adapted to bring about the specified target substance's rapid oxidation. The minimum temperature for rapid formation of oxides is codependent on the specific target substance and MOS material involved.

The cycling which is required for practice of the invention is effected by varying the supply of power for the heating element, and in turn varying the amount of heat energy provided to the MOS material. Thus, in a typical cycle the sensor is thermally oscillated by electrical heating in a known manner. A suitable element of conventional nature (e.g., a commercially available heater unit) is furnished with a supply of power sufficient to drive the temperature of the MOS material to one at or above the minimum temperature at which rapid oxide formation takes place. The MOS material can if desired be heated to a temperature less than the aforementioned minimum temperature but high enough to bring the material to a state of equilibrium between the target substance and the oxidation product or products thereof. But whether the MOS material is at such equilibrium temperature or below it, the power source must be able to elevate the MOS material's temperature to the "minimum" one required for rapid formation of oxides. Thereafter the supply is decreased or paused so that the temperature drops below the rapid oxide formation level. The power source is one which can be selected from among many that are known in and of themselves, and are readily adapted to use in the invention relying on conventional know-how of their working and the teaching herein.

Circuitry, such as a processor, commands that electrical power be relayed through one or more interconnections to a heating element. The amount of such power is that gauged to be sufficient for causing the element to emit (at a range of levels or alternatively to refrain from emitting) heat energy in line with the desired outcome, when the MOS material is in the presence of (among other things potentially) oxygen and a target substance such as hydrogen or a compound containing a carbon and hydrogen bond. Power is applied to the MOS material. Accordingly, by way of illustration, the aforementioned circuitry (optionally including one or more adjunctive components, such as a transistor) triggers the heating element to behave in such manner that the MOS material, which is in an environment containing a target substance, has a temperature whereat the target substance is adsorbed on the MOS material. The conductivity of the MOS material can be continually monitored and a signal representative of that conductivity detected. At a pre-determined time, the circuitry (e.g., processor) brings about an increase in the amount of power supplied to the heating element, whereby the amount of heat energy emitted by the element causes the MOS material to increase to a temperature at or above the aforementioned certain temperature, e.g., the minimum temperature for rapid oxidation formation.

Again, the conductivity of the MOS material is radically increased in a very short time when the target substance adsorbed on the material is rapidly oxidized at or above the minimum temperature for rapid oxide formation. The spiking conductivity can be measured at its peak over a very brief duration of time because of the very high rate at which the conductivity increases. The signal corresponding to conductivity detected within this very narrow window of time is referred to herein as a transient signal. Detection is effected by circuitry, such as a processor, that records and stores the conductivity values during cycling of the power source and heating element, including the maximum conductivity value which corresponds to the aforementioned transient signal. Since the duration of the transient signal is brief, a timer in the circuitry—which is coordinated with the anticipated duration of time required for generation of the transient signal—causes the relevant circuitry to interrupt the supply of power, or to decrease below that necessary for rapid oxide formation. When the power is discontinued or decreased, the heating element gives off commensurately less heat energy, and the temperature of the MOS material is permitted to decrease to a level below that at which rapid oxide formation occurs.

The aforementioned determinations of conductivity of the MOS material can be made over the course of various preselected intervals, which intervals correspond with a period when the temperature is below the minimum one at which rapid oxide formation occurs, e.g. (though not necessarily), when there is equilibrium at the baseline temperature (a "cool interval"), a period when the transient signal occurs (a "hot interval"), and a period when the MOS material's temperature is again below that at which rapid oxide formation occurs (a "cool interval") such as (but not necessarily) the baseline temperature. The interval for monitoring the transient signal can be shorter than would conventionally be the case because the transient signal occurs in a compressed time frame far less than the interval for measuring the signal at the baseline or other temperature below the one at which rapid formation of oxides occurs. By reason of the interconnection of the MOS material and relevant circuitry, the signals generated at the MOS material relating to conductivity are detected, and (on the one hand) the signal representative of the conductivity during the interval at the baseline or other temperature below that for rapid oxide formation and (on the other hand) the transient signal are subjected to a differential comparison. Such comparison gives rise to a further and derivative signal which is representative of the concentration of the preselected target substance.

The elements of the inventive sensor system are in and of themselves conventional. Thus, suitable technology is available separately and respectively for: (i) measuring conductivity or other property of the MOS material to determine its change with temperature; (ii) heating the MOS material; (iii) generating power to make the heating element operative; (iv) oscillating such power in accordance with a preselected pattern; (v) converting the measurement of conductivity (or other measured property) to a signal which is readable by circuitry in preparation for comparing the signal with other like-derived signals, said circuitry being capable of performing a differential comparison of a plurality of said signals and of generating a further signal which is representative of the difference between said compared signals; and (vi) synthesizing from the further signal a quantitation of the concentration of the target substance; as well as (vii) transducing one type of energy to another and (viii) electronically interconnecting the functions which together comprise the invention. Such devices and operations being individually well-known in the art, they need not be shown and/or described in detail herein.

The invention's versatility is manifest in the range of circuitry options which are suitable for utilization in its practice. Therefore, the invention can be implemented with digital circuitry or analog circuitry. The circuitry can be separated into modular units, on a task-by-task basis, or can be partially integrated so that—while certain portions dedicated to a specialized task are separately configured—other portions which are not task-specific can be interconnected with task-specific portions, so the non-specific portions can be multiple-use in nature. In a preferred embodiment, the circuitry or one or more portions thereof are packaged in a processor, which can be modular (by task) or multi-purpose. For instance, a unitary processor can contain circuitry for one or more of oscillating the heating element, sensing conductivity (or other desired property), ascertaining temperature, differentially comparing conductivity values, synthesizing a further signal representative of the difference, and converting such further signal to a concentration value for the target substance.

The circuitry can be designed to apply one or more algorithms, acting in a unified manner along with the invention's other elements, to ascertain the concentration parameter ultimately sought. Accordingly, a microprocessor-based data analysis system can be used. A metal-oxide gas sensor produces an analog signal which is converted to a digital signal by an analog-to-digital converter and stored in a microprocessor. The microprocessor is clocked by a timer for memory refreshing and other purposes. Digital data may then be sampled by the microprocessor to effect detection of conductance peaks or valleys, derivation of conductance ratios, or implementation of other conductance pattern recognition techniques, using well-known algorithms. By way of example, an algorithm for peak detection would involve use of an equation for the derivative of conductance. When the derivative is zero, conductance is at a peak or valley, and either can be selected. Once peaks and valleys are determined, the time of occurrence may be measured relative to a point in the thermal cycle, such as the heater turnoff time or t=0. Alternatively, other slope detection techniques can be used. This data correlates with a methodology for identifying a gas concentration level.

The precursor methodology for practice of the invention involves initially calibrating the innovative sensor system. Calibration is important in order to establish a foundation for accurate measurement. Even though a central purpose of the invention is to mitigate the effects of drift to influence the reliability of MOS material-based sensor operation, it is still basic to satisfactory sensing operations to begin from a well-founded and uncompromised determination of conductivity and in turn target-substance concentration.

More specifically, MOS materials need some time to "warm up" and stabilize. Many MOS materials have cross-sensitivities to non-target substances. If the target is methane and the selected sensor has a cross-sensitivity to alcohol, even an incidental exposure to an alcohol in the surrounding environment can provoke an alarm. So, for instance, in fuel cell applications, the MOS material utilized for a specific fuel gas is preferably selected with this cross-sensitivity in mind.

In addition to the foregoing, this cross-sensitivity causes additional problems at startup because high-molecular-weight volatile organic compounds (VOC) can deposit onto the sensor element while the fuel cell is off (and the sensor element is cold). Upon startup, these same volatile organic compounds begin to decompose and evaporate. As a result, the sensor can sense these by-products and can output false positive alarms upon startup. And, though the sensor element may reach operating temperature within about a minute, it can take several minutes to boil off or decompose stubborn volatile organic compounds and obtain a stable reading which can be deemed justifiably reliable.

Thus, in addition to the benefit of decreasing or eliminating the need for dealing with a relatively inaccessible sensor system (and the included MOS material), practice of the invention confers the further advantage that the time when the sensing operation is "down" due to re-zeroing and other recalibration is decreased, because the frequency of re-zeroing and re-calibration events is decreased.

Moreover, MOS gas sensors are used for many industrial applications, such as in fuel cell systems that utilize fuels which are potentially explosive. The invention's practice is especially advantageous because it enables the invention's practitioner to take accurate readings with little interruption. As can readily be appreciated, when there is an enhanced, precise and frequent determination of the concentration of a target substance, as is conferred with the invention, the chances for under-measurement of dangerous substances are decreased. With practice of the invention, the chances for accumulation of an undetected dangerous substance are lowered.

Calibration in support of the invention's practice is carried out in accordance with known procedures. The MOS material and sensor system in which it is incorporated can be primed as follows:
1. exposing the MOS material sensor to a range of known target substance concentrations, said substance being of a type measurable by the sensor;
2. thermally cycling the sensor for each concentration, the thermal cycle having a heating interval and a cooling interval; and
3. measuring the conductivity of the MOS material at each concentration, converting that parameter to a corresponding concentration, and correlating same with the known concentration.

The circuitry which commands the power applied to the heating element provides a signal with positive, generally-rectangular pulses defining times during which the heater alternately (i) causes the MOS material to rise from a temperature below to one at not less than the minimum temperature for rapid formation of oxides, and then (ii) allows the temperature of the MOS material to cool down below the temperature at which rapid oxide formation occurs. The square-wave or rectangular-wave heater modulation can be in other waveforms, e.g., sine-wave, triangle-wave, etc., but the ratios which can be utilized are the same as disclosed herein. The oscillation or cycling of the power applied to the heating element, measurement of the temperature of the MOS material, and ascertainment of conductivity of such material, are frequently (though not necessarily) repeated continually while the sensing activities are underway.

In an especially helpful embodiment of the invention, the sensing of the target substance's concentration is coupled with a warning feature which gives an alert when such concentration reaches or exceeds a predetermined level. By way of example, when there is a differential comparison of the signals generated respectively during the heating interval and the cooling interval and a product signal derived, the latter is relayed to circuitry (either integral with the other circuitry, or separate from and adjunctive thereto) which causes an alarm to be emitted. The alarm can be visual and/or aural.

The MOS material is typically (though not necessarily) located within a confined space, so that the environment being analyzed for target substance concentration is uniform from one measurement event to another. In the event the space being sampled, for instance one in which the sensor system is located in a conduit of reasonably limited cross-section or compartment of reasonably manageable volume, the MOS material need not be located in a chamber dedicated to protection of the environment from distortion by unrepresentative dilution or other alteration of the target substance's concentration. Rather, the conduit or compartment is preferably sufficiently limited in cross-section or volume that unrepresentative dilution or other alteration of the aforementioned concentration is not material. On the other hand, as a hedge against undesirable alteration, the MOS material can be located within a space constituting a cavity or defined by a housing or other structure, into which space the environment to be analyzed is drawn or flows, and in which space the environment is shielded.

In a preferred aspect, the invention is in a sensor system for ascertaining the concentration of a preselected target substance, said system having a mitigated tendency for yielding results distorted by the departure from a state of calibration, which comprises a sensor including a metal oxide semiconductor material residing in a confined space suitable for containing said target substance, which material is interactive with said preselected target substance at a minimum temperature resulting in rapid formation of one or more oxides of said target substance, whereby a change in conductivity of the material also occurs;

an element for heating the metal oxide semiconductor material, said element being located such that upon command it is capable of bringing about a modulation of the material's temperature from one at which said rapid oxide formation does not take place, to one at or above said minimum temperature at which rapid oxide formation does take place;

circuitry for emitting a signal at a predetermined time, which signal activates provision from a power source interconnected with said circuitry of output to cause said heating element to bring about modulation of said material's temperature from one at which rapid oxide formation does not take place to one at or above said minimum temperature at which rapid oxide formation does take place, such that a precursor mode of sensor operation endures up until the time said material's temperature reaches the minimum one at which rapid oxide formation takes place, and for further emitting another signal at a subsequent predetermined time which other signal changes the output from said power source to cause said heating element to behave in a manner permitting said material's temperature to decrease below the minimum one at which rapid oxide formation takes place, such that a measurement mode of sensor operation endures up until the time said material's temperature decreases below the one at which rapid oxide formation takes place, the material's being capable of temperature change sufficiently rapid that the duration elapsing between said predetermined time and said subsequent predetermined time can be short enough that the effect of any substantial departure from the sensor system's state of calibration is obviated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid oxide formation and a corresponding increase in conductivity of the metal oxide semiconductor material to occur;

said power source, or an alternative power source, being interconnected with the metal oxide semiconductor material such that a current can be generated in, and a signal representing the material's conductivity provided by, the material;

circuitry for detecting a signal representative of the conductivity of the metal oxide semiconductor material during the precursor mode of sensor operation, and for detecting another signal representative of the conductivity of said material during the measurement mode of sensor operation; and circuitry for performing a differential comparison of said respective detected signals to derive a further signal representative of the target substance concentration.

In another preferred aspect, the invention is in a method of mitigating the distortion of results from a sensor system for ascertaining the concentration of a preselected target substance, said distortion stemming from the sensor system's departure from a state of calibration, which comprises providing a metal oxide semiconductor material located in a confined space, which material is interactive with said preselected target substance at a minimum temperature resulting in rapid formation of one or more oxides of said target substance, whereby a change in conductivity of the material also occurs;

further providing an element for heating the metal oxide semiconductor material, said element being located such that upon command it is capable of bringing about a modulation of the material's temperature from one at which said rapid oxide formation does not take place, to one at or above said minimum temperature at which rapid oxide formation does take place;

enabling a determination of the target substance's concentration through (i) interconnection of the heating element and circuitry configured to emit a signal at a predetermined time, which signal activates provision from a power source interconnected with said circuitry to cause said heating element to bring about the metal oxide semiconductor material's temperature to be modulated from one at which rapid oxide formation does not take place to one at or above that at which rapid oxide formation does take place, such that a precursor mode of sensor operation endures up until the time said material's temperature reaches the minimum one at which rapid oxide formation takes place, and for further emitting another signal at a subsequent predetermined time which other signal changes the output from said power source to cause said heat element to behave in a manner permitting said material's temperature to decrease below the minimum one at which rapid oxide formation takes place, such that a measurement mode of sensor operation endures up until the time said material's temperature decreases below the one at which rapid oxide formation takes place, the material's being capable of temperature change sufficiently rapid that the duration of time elapsing between said predetermined time and said subsequent predetermined time can be short enough that the effect of any substantial departure from the sensor system's state of calibration is obviated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid oxide formation and a corresponding increase in conductivity of the metal oxide semiconductor material to occur;

(ii) interconnection of said metal oxide semiconductor material and said power source, or an alternative power source, whereby to generate current in, and provide a signal representative of the conductivity of, the metal oxide semiconductor material during the precursor mode of sensor operation, and for generating current in, and providing another signal representative of the conductivity of, said material during the measurement mode of sensor operation;

(iii) interconnection of said metal oxide semiconductor with circuitry for detecting the signal provided during the precursor mode of sensor operation, and for detecting another signal provided during the measurement mode of sensor operation; and (iv) interconnection of said detection circuitry with circuitry capable of performing a differential comparison of said respective detected signals to derive yet another signal representative of the target substance concentration.

And, in yet a further preferred aspect, the invention is in a method of mitigating the distortion of results from a sensor system for ascertaining the concentration of a preselected target substance, which distortion stems from the sensor system's departure from a state of calibration, said sensor system including a metal oxide semiconductor material which is interactive with said preselected target substance at a minimum temperature resulting in rapid formation of one or more oxides of said target substance, whereby a change in conductivity of the material also occurs, which method comprises contacting said metal oxide semiconductor material with said preselected target substance in a confined space for containing said target substance;

at a predetermined time during the contact between the metal oxide semiconductor material and the preselected target substance, applying power to a heating element whereby said material's temperature is modulated from one below the minimum temperature at which rapid oxide formation occurs to one at or above said minimum temperature at which rapid oxide formation occurs for a period sufficient that rapid oxidation of the target substance is effected, such that a precursor mode of sensor operation endures up until the time said material's temperature reaches the minimum one at which rapid oxide formation takes place, and at a subsequent predetermined time during the contact between the metal oxide semiconductor material and the preselected target substance decreasing the application of power to the heating element whereby the temperature of said material is permitted to modulate from one at or above said minimum temperature at which rapid oxide formation occurs to one less than the minimum temperature at which rapid oxide formation occurs, such that a measurement mode of sensor operation endures up until the time said material's temperature decreases below the one at which rapid oxide formation takes place, the material being allowed to endure at said lesser temperature for a period sufficient that said oxidation is substantially paused, the material's being capable of temperature change sufficiently rapid that the duration elapsing between said predetermined time and said subsequent predetermined time can be short enough that the effect of any substantial departure from the sensor system's state of calibration is obviated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid oxide formation and a corresponding increase in conductivity of the metal oxide semiconductor material to occur;

applying power to said metal oxide whereby to generate a signal representative of the conductivity of the metal oxide semiconductor material during the precursor mode of sensor operation, and another signal representative of the conductivity of the metal oxide semiconductor material during the measurement mode of sensor operation;

detecting the signal generated during the precursor mode of sensor operation, and the other signal generated during the measurement mode of sensor operation; and performing a differential comparison of said signals to derive yet another signal representative of the target substance concentration.

By way of providing an example of the invention, in FIG. 1 a sensor system 1 in accordance with the invention is depicted schematically. Incorporated in the sensor system are a sensor 3 comprising an MOS material in tandem with a resistive heating element 5. The sensor system is exposed in a confined space created by a housing 15 (shown by dashed lining) to zero-air and alternatively an atmosphere which is zero-air in combination with isobutylene in a concentration of 500 ppm. The heating element is powered by current which is generated by subjecting the heating element to a voltage supplied by element 7. The current is oscillated between "on" and "off" by the operation of transistor 11 which is interconnected with the heating element and with a unit 9 which includes circuitry packages in the nature of respectively a microcontroller and a signal processor. The microcontroller circuitry furnishes signals to the transistor 11 which directs it to permit or interrupt current flow to the heating element whereby the heating element either emits heat energy or not, as the case may be. In addition, element 7 is interconnected with sensor 3 comprising the MOS material. Due to the subjecting of the sensor to the aforementioned voltage, current flows through the MOS material.

As a consequence of the heating element 7's location in proximity of sensor 3, the temperature of the MOS material varies with the heating element's behavior: when the heating element is operational, the temperature of the MOS material rises to or above the minimum one at which rapid formation of oxides of any target substance adsorbed on the MOS material takes place; when the heating element is not operational, the MOS material cools to a temperature below the minimum temperature for rapid oxide formation. The microcontroller circuitry of unit 9 directs the transistor 11 to interrupt current flow to the heating element 5 for a period of five (5) seconds which causes the heating element's emitted heat energy to fade such that the temperature of the MOS material decreases in temperature, a time period that is enough for the accumulation of an amount of target substance sufficient to support a "burn-off" (i.e., the rapid formation of oxides) of such adsorbed target substance effective to generate a transient signal. Then, the microcontroller circuitry of unit 9 directs the transistor to permit current flow to the heating element, such that the heating element's emission of heat energy increases along with the conductivity of the MOS material. A reaction between the target substance adsorbed on the MOS material and oxygen from the MOS material, to form oxides of the target substance, occurs in a highly accelerated time frame due to the high temperature of the material. An analog signal corresponding to the conductivity at temperature below the minimum one for rapid oxide formation, and another analog signal corresponding to the conductivity at or above said minimum temperature, the transient signal, occur and are turned into a digital signal by converter circuitry 13. The digital signal outputted from converter circuitry 13 is received by the signal processor circuitry of unit 9.

The digital signals outputted from converter circuitry 13, for respectively conductivity of the MOS material at temperature less than the minimum one at which rapid oxide formation occurs, and conductivity represented by the transient signal, are stored in the signal processor circuitry of unit 9. They then undergo a differential comparison imposed by an algorithm programmed into the processor. The algorithm computes a new signal which represents, after the surplus concentration indication introduced by burn-off is removed by way of compensation, is further processed by the relevant circuitry to yield a target-substance concentration value which by the same token reveals information about the quantity of the target substance present. This new signal is in digital form, and can be subject to additional processing, tailored to the particular needs of the practitioner if desired. Moreover, the new digital signal is optionally passed through line 17 to converter 19 where it is turned into analog format. The analog signal is then passed through line 21 to further circuitry (conventional, and not shown for the purpose of simplicity) where additional processing is performed, once again tailored to the particular needs of the practitioner.

Figure 2:
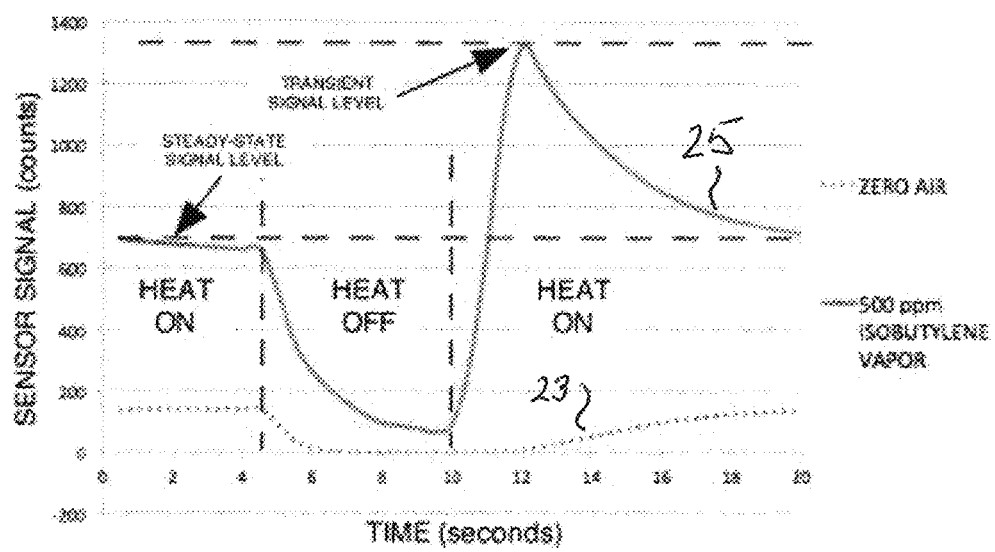
FIG. 2 is a plot of signals from, respectively, a sensor system in the presence of a hydrocarbon according to the invention, and a similar sensor system not in the presence of a hydrocarbon, each against time.

FIG. 2 charts the signal produced by the system of FIG. 1 (in counts) against time (in seconds). The signal generated when MOS material 3 is exposed to zero-air is portrayed via dotted line 23. The signal generated when MOS material 3 is exposed to the mixture of zero air and isobutylene is portrayed via a solid line 25. In zero air, no transient signal is produced. Instead, the signal moves from a steady-state value characteristic of the bulk conductivity of the hot MOS material to a very low value typical of a cold MOS material, and back. On the other hand, in the presence of the isobutylene component, there is a very large transient signal which ultimately converges back to a steady-state value significantly higher than the steady-state value observed in zero air.

Thus, a sensor and a method for quantitating a target substance with an MOS sensor have been provided.

In compliance with the statute, the invention has been described in language that enables practice of the invention. It is to be understood, however, that the invention is not limited to the specific features shown and described. The invention is, therefore, claimed in any of its forms or modifications within the proper scope of the appended claims appropriately interpreted in accordance with the doctrine of equivalents.

The invention claimed is:

1. A sensor system for ascertaining the concentration of a preselected target substance, said system having a mitigated tendency for yielding results distorted by the departure from a state of calibration, which comprises a metal oxide semiconductor material which is interactive with said preselective target substance whereby, when said material reaches a certain temperature, there is a rapid formation of oxides of the target substance;

an element, in operative association with the metal oxide semiconductor material, which element is capable of giving off heat energy sufficient to cause the metal oxide semiconductor material to reach or exceed said certain temperature;

circuitry for emitting a signal at a predetermined time which initiates the powering of the element to increase its output of heat energy such that the temperature of the metal oxide semiconductor material increases from one below said certain temperature to one at or above said certain temperature, and for further emitting another signal at a subsequent predetermined time, which other signal initiates the depowering of the element to decrease its output of heat energy such that the metal oxide semiconductor material's temperature is permitted to decrease from one at or above said certain temperature to one below said certain temperature, the duration elapsing while the metal oxide semiconductor material is below said certain temperature being such that if present target substance is adsorbed on said metal oxide semiconductor material in an amount effective to support said rapid oxidation formation, and the duration elapsing while the metal oxide semiconductor material is at or above said certain temperature being such that adequate opportunity is afforded for said rapid oxide formation to occur;

circuitry for detecting a signal representative of the conductivity of the metal oxide semiconductor material during the time the temperature of said material is below said certain temperature, and for detecting another signal representative of the conductivity of the metal oxide semiconductor material during the time the temperature of said material is at or above said certain temperature; and circuitry for performing a differential comparison of said respective detected signals to derive a further signal representative of the target substance concentration.

2. A sensor system as defined in claim 1, wherein the metal oxide semiconductor material is selected from the group consisting of tin oxide, zinc oxide and tungsten oxide.

3. A sensor system as defined in claim 1, wherein the circuitry for providing a signal to the heating element is configured such that it causes a behavior of the heating element which brings about a temperature of the metal oxide semiconductor material in the range of from 0 to 100° C. in the duration elapsing while said material is below said certain temperature.

4. A sensor system as defined in claim 1, wherein the circuitry for providing a signal to the heating element is configured such that it causes a behavior of the heating element which brings about a temperature of the metal oxide semiconductor material in the range of from 200 to 450° C. in the duration elapsing while said material is at or above said certain temperature.

5. A sensor system as defined in claim 1, wherein the circuitry for emitting a signal at a predetermined time is interconnected with a power source, which signal activates provision from the power source of an output to cause said heating element which is interconnected with said power source to bring about modulation of said material's temperature from one at which rapid oxide formation does not take place to one at or above said minimum temperature at which rapid oxide formation does take place, such that a precursor mode of sensor operation endures up until the time said material's temperature reaches the minimum one at which rapid oxide formation takes place, and for further emitting another signal at a subsequent predetermined time which other signal interrupts provision of output from said power source to cause said heating element to behave in a manner permitting said material's temperature to decrease below the minimum one at which rapid oxide formation takes place, such that a measurement mode of sensor operation endures up until the time said material's temperature decreases below the one at which rapid oxide formation takes place.

6. A sensor system as described in claim 1, wherein the MOS material is interactive with a target substance selected from the group consisting of hydrogen, hydrocarbons, alcohols, aldehydes, ketones, acids, esters, ethers, and cyclic species, whether saturated or unsaturated, and whether or not containing hetero atoms.

7. A method of mitigating the distortion of results from a sensor system for ascertaining the concentration of a preselected target substance, said distortion stemming from the sensor system's departure from a state of calibration, which comprises providing a metal oxide semiconductor material which is interactive with a preselected target substance whereby, when said material reaches a certain temperature, there is a rapid formation of oxides of the target substance;

further providing an element, located in operative association with the metal oxide semiconductor material, which element is capable of giving off heat energy sufficient to cause the metal oxide semiconductor material to reach or exceed said certain temperature; and enabling a determination of the target substance's concentration through (i) interconnection of the element with circuitry for emitting a signal at a predetermined time, which signal initiates the powering of the element to increase its output of heat energy such that the temperature of the metal oxide semiconductor material increases from one below said certain temperature, and for further emitting another signal at a subsequent predetermined time, which other signal initiates the depowering of the element to decrease its output of heat energy such that the metal oxide semiconductor material's temperature is permitted to decrease from one at or above said certain temperature to one below said certain temperature, the duration elapsing while the metal oxide semiconductor material is below said certain temperature being such that if present target substance is adsorbed on said metal oxide semiconductor material in an amount effective to support said rapid oxidation formation, and the duration elapsing while the metal oxide semiconductor material is at or above said certain temperature being such that adequate opportunity is afforded for such rapid oxide formation to occur;

(ii) interconnection of the metal oxide semiconductor material with circuitry capable of detecting a signal provided during the time the temperature of the metal oxide semiconductor material is below said certain temperature, and for detecting another signal representative of the conductivity of the metal oxide semiconductor material during the time the temperature of said material is at or above said certain temperature; and (iii) interconnection of said detection circuitry with circuitry capable of performing a differential comparison of said respective detected signals to derive yet another signal representative of the target substance concentration.

8. A method as defined in claim 7, wherein the metal oxide semiconductor material is selected from the group consisting of tin oxide, zinc oxide and tungsten oxide.

9. A method as defined in claim 7, which further comprises causing the heating element to behave such that the temperature of the metal oxide semiconductor material is from 0 to 100° C. in the duration while the material is below said certain temperature.

10. A method as defined in claim 7, which further comprises causing the heating element to behave such that the temperature of the metal oxide semiconductor material is from 200 to 450° C. in the duration while the material is at or above said certain temperature.

11. A method as defined in claim 7, which further comprises interconnection of circuitry for emitting a signal at a predetermined time and a power source, which signal activates provision from the power source interconnected with said circuitry to cause said heating element to bring about the metal oxide semiconductor material's temperature to be modulated from one at which rapid oxide formation does not take place to one at or above that at which rapid oxide formation does take place, such that a precursor mode of sensor operation endures up until the time said material's temperature reaches the minimum one at which rapid oxide formation takes place, and for further emitting another signal at a subsequent predetermined time, which other signal changes the output from said power source to cause said heat element to behave in a manner permitting said material's temperature to decrease below the minimum one at which rapid oxide formation takes place, such that a measurement mode of sensor operation endures up until the time said material's temperature decreases below the one at which rapid oxide formation takes place.

12. A method as defined in claim 7, wherein the MOS material is interactive with a target substance selected from the group consisting of hydrogen, hydrocarbons, alcohols, aldehydes, ketones, acids, esters, ethers, and cyclic species, whether saturated or unsaturated, and whether or not containing hetero atoms.

13. A method of mitigating the distortion of results from a sensor system for ascertaining the concentration of a preselected target substance, which distortion stems from the sensor system's departure from a state of calibration, said sensor system including a metal oxide semiconductor material which is interactive with said preselected target substance at or above a certain temperature resulting in rapid formation of one or more oxides of said target substance, whereby a change in conductivity of the material also occurs, which method comprises
   contacting said metal oxide semiconductor material with said preselected target substance;
   at a predetermined time during the contact between the metal oxide semiconductor material and the preselected target substance, heating said material such that its temperature increases from one below said certain temperature to one at or above said certain temperature, the duration elapsing while the material is below said certain temperature being such that if present target substance is adsorbed on said metal oxide semiconductor material in an amount effective to support said rapid oxide formation;
   at a subsequent predetermined time during the contact between the metal oxide semiconductor material and the preselected target substance, permitting the temperature to decrease from one at or above said certain temperature to one below said certain temperature, the duration elapsing while the material is at or above said certain temperature being such that adequate opportunity is afforded for said rapid oxide formation to occur;
   generating a signal representative of the conductivity of the metal oxide semiconductor material while the material is below said certain temperature;
   generating another signal representative of the conductivity of the metal oxide semiconductor material while the material is at or above said certain temperature;
   detecting the conductivity-representative signal generated while the material's temperature is below said certain temperature;
   detecting the conductivity-representative signal generated while the material's temperature is at or above said certain temperature; and
   performing a differential comparison of said respective detected signals to derive a further signal representative of the target substance concentration.

14. A method as defined in claim 13, wherein the metal oxide semiconductor material is selected from the group consisting of tin oxide, zinc oxide and tungsten oxide.

15. A method as defined in claim 13, which further comprises causing the temperature of the metal oxide semiconductor material to be from 0 to 100° C. in the duration elapsing while the material is below said certain temperature.

16. A method as defined in claim 13, which further comprises causing the temperature of the metal oxide semiconductor material to be from 200 to 450° C. in the duration elapsing while the material is at or above said certain temperature.

17. A method as defined in claim 13, which further comprises applying power to a heating element whereby said material's temperature is modulated from one below the minimum temperature at which rapid oxide formation occurs to one at or above said minimum temperature at which rapid oxide formation occurs for a period sufficient that rapid oxidation of the target substance is effected, such that a precursor mode of sensor operation endures up until the time said material's temperature reaches the minimum one at which rapid oxide formation takes place and, at a subsequent predetermined time during the contact between the metal oxide semiconductor material and the preselected target substance, decreasing the application of power to the heating element whereby the temperature of said material is permitted to modulate from one at or above said minimum temperature at which rapid oxide formation occurs to one less than the minimum temperature at which rapid oxide formation occurs, such that a measurement mode of sensor operation endures up until the time said material's temperature decreases below the one at which rapid oxide formation takes place.

18. A method as defined in claim 13, wherein the MOS material is interactive with a target substance selected from the group consisting of hydrogen, hydrocarbons, alcohols, aldehydes, ketones, acids, esters, ethers, and cyclic species, whether saturated or unsaturated, and whether or not containing hetero atoms.

19. A sensor system for ascertaining a concentration of a preselected target substance, said system having a mitigated tendency for yielding results distorted by the departure from a state of calibration, which comprises
   a sensor including a metal oxide semiconductor material, which material is interactive with said preselected target substance at a minimum temperature resulting in rapid formation of one or more oxides of said target substance, whereby a change in conductivity of the material also occurs;
   an element for heating the metal oxide semiconductor material, said element being located such that it is capable of bringing about a modulation of the material's temperature from one at which said rapid formation of oxides does not take place, to one at or above said minimum temperature at which rapid oxide formation does take place;

circuitry for emitting a signal at a predetermined time, which signal initiates manipulation of said heating element's behavior to modulate said material's temperature from one at which rapid oxide formation does not take place to one at or above said minimum temperature at which rapid oxide formation does take place, such that a precursor mode of sensor operation endures up until the time said material's temperature reaches the minimum one at which rapid oxide formation takes place, and for further emitting another signal at a subsequent predetermined time, which other signal manipulates said heating element's behavior to permit said material's temperature to decrease below the minimum one at which rapid oxide formation takes place, such that a measurement mode of sensor operation endures up until the time said material's temperature decreases below the one at which rapid oxide formation takes place, the material being capable of temperature change sufficiently rapid that the duration elapsing between said predetermined time and said subsequent predetermined time is short enough that the effect of any substantial departure from the sensor system's state of calibration is negated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid formation of oxides and a corresponding increase in conductivity of the metal oxide semiconductor material to take place;

circuitry for detecting a signal representative of the conductivity of the metal oxide semiconductor material during the precursor mode of sensor operation, and for detecting another signal representative of the conductivity of said material during the measurement mode of sensor operation; and circuitry for performing a differential comparison of said respective detected signals to derive a further signal representative of the target substance concentration.

20. A method of mitigating distortion of results from a sensor system for ascertaining a concentration of a preselected target substance, said distortion stemming from the sensor system's departure from a state of calibration, which comprises providing a metal oxide semiconductor material, which material is interactive with said preselected target substance at a minimum temperature resulting in rapid formation of one or more oxides of said target substance, whereby a change in conductivity of the material also occurs;

further providing an element for heating the metal oxide semiconductor material, said element being located such that it is capable of bringing about a modulation of the material's temperature from one at which said rapid oxide formation does not take place, to one at or above said minimum temperature at which rapid oxide formation does take place; and enabling a determination of the target substance's concentration through (i) interconnection of the heating element and circuitry, wherein the circuitry is configured to emit a signal at a predetermined time, which signal initiates manipulation of said heating element's behavior to modulate said material's temperature from one at which rapid oxide formation does not take place to one at or above said minimum temperature at which rapid oxide formation does take place, such that a precursor mode of sensor operation endures up until the time said material's temperature reaches the one at which rapid oxide formation takes place, and for further emitting another signal at a subsequent predetermined time which other signal initiates manipulation of said element's behavior to permit said material's temperature to decrease from one at or above which rapid oxide formation does take place to one at which rapid oxide formation does not take place, such that a measurement mode of sensor operation endures up until the time said material's temperature decreases below the one at which rapid oxide formation takes place, the material being capable of temperature change sufficiently rapid that the duration of time elapsing between said predetermined time and said subsequent predetermined time is short enough that the effect of any substantial departure from the sensor system's state of calibration is negated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid oxide formation and a corresponding increase in conductivity of the metal oxide semiconductor material to occur;

(ii) interconnection of said metal oxide semiconductor material and said power source, or an alternative power source, whereby to generate current in, and provide a signal representative of the conductivity of the metal oxide semiconductor material during the precursor mode of sensor operation, and generate a current in, and provide a further signal representative of the conductivity of said material during the measurement mode of sensor operation; and (iii) interconnection of said material with circuitry capable of detecting the signal provided during the precursor mode of sensor operation, and the further signal provided during the measurement mode of sensor operation; and (iv) interconnection of said detection circuitry with circuitry capable of performing a differential comparison of said respective detected signals to derive yet another signal representative of the target substance concentration.

21. A method of mitigating distortion of results from a sensor system for ascertaining a concentration of a preselected target substance, which distortion stems from the sensor system's departure from a state of calibration, said sensor system including a metal oxide semiconductor material which is interactive with said preselected target substance at a minimum temperature resulting in rapid formation of one or more oxides of said target substance, whereby a change in conductivity of the material also occurs, which method comprises contacting said metal oxide semiconductor material with said preselected target substance;

at a predetermined time during the contact between the metal oxide semiconductor material and the preselected target substance, heating said material such that its temperature is modulated from one below the minimum temperature at which rapid oxide formation occurs to one at or above said minimum temperature at which rapid oxide formation occurs for a period sufficient that rapid oxidation of the target substance is effected, such that a precursor mode of sensor operation endures up until the time said material's temperature reaches the one at which rapid oxide formation takes place and, at a subsequent predetermined time during the contact between the metal oxide semiconductor material and the preselected target substance, permitting the temperature of said material to modulate from one at or above said minimum temperature at which rapid oxide formation occurs to one less than the minimum temperature at which rapid oxide formation occurs, such that a measurement mode of sensor operation endures up until the time said material's temperature decreases below the one at which rapid oxide formation takes place, the material being capable of temperature change sufficiently rapid that the duration elapsing between said predetermined time and said subsequent predetermined time is short enough that the effect of any substantial departure from the sensor system's state of calibration is negated, the duration of said precursor mode being such that if present target substance is adsorbed on said metal oxide semiconductor material in adequate amount to support said rapid oxidation formation at said minimum temperature, and the duration of said measurement mode being sufficient that an adequate opportunity is afforded for said rapid oxide formation and a corresponding increase in conductivity of the metal oxide semiconductor material to occur;

generating a signal representative of the conductivity of the metal oxide semiconductor material during the precursor mode of sensor operation, and another signal representative of the conductivity of the metal oxide semiconductor material during the measurement mode of sensor operation;

detecting the signal generated during the precursor mode of sensor operation, and the other signal generated during the measurement mode of sensor operation; and performing a differential comparison of said respective detected signals to derive a further signal representative of the target substance concentration.

* * * * *